US012564662B2

(12) United States Patent
Holenstein et al.

(10) Patent No.: US 12,564,662 B2
(45) **Date of Patent: \*Mar. 3, 2026**

(54) DISPOSABLE SYSTEM AND METHOD FOR PREPARING A COMPRESSED HYDROGEL

(71) Applicant: CUTISS AG, Schlieren (CH)

(72) Inventors: Claude Nicolas Holenstein, Zurich (CH); Jerry Donnan, Edinburgh (GB); Vincent Ronfard, Villarzel (CH)

(73) Assignee: Cutiss AG, Schlieren (CH)

( * ) Notice: Subject to any disclaimer, the term of this patent is extended or adjusted under 35 U.S.C. 154(b) by 564 days.

This patent is subject to a terminal disclaimer.

(21) Appl. No.: 17/907,989

(22) PCT Filed: Mar. 1, 2021

(86) PCT No.: PCT/IL2021/050225
§ 371 (c)(1),
(2) Date: Aug. 30, 2022

(87) PCT Pub. No.: WO2021/176443
PCT Pub. Date: Sep. 10, 2021

(65) Prior Publication Data
US 2023/0114908 A1 Apr. 13, 2023

Related U.S. Application Data

(60) Provisional application No. 62/983,791, filed on Mar. 2, 2020.

(51) Int. Cl.
| | |
|---|---|
| *A61L 27/52* | (2006.01) |
| *A61L 27/24* | (2006.01) |
| *A61L 27/38* | (2006.01) |
| *A61L 27/60* | (2006.01) |

(52) U.S. Cl.
CPC ............... *A61L 27/52* (2013.01); *A61L 27/24* (2013.01); *A61L 27/3813* (2013.01); *A61L 27/60* (2013.01)

(58) Field of Classification Search
CPC ...... A61L 27/52; A61L 27/24; A61L 27/3813; A61L 27/60; A61L 27/3804; C12M 25/14; C12M 21/08; C08L 89/06
See application file for complete search history.

(56) References Cited

U.S. PATENT DOCUMENTS

2016/0136333 A1 * 5/2016 Reichmann

OTHER PUBLICATIONS

PCT International Search Report and Written Opinion, PCT Application No. PCT/IL2021/050225, Jun. 7, 2021, 9 pages.
Braziulis, E., et al., "Modified Plastic Compression of Collagen Hydrogels Provides an Ideal Matrix for Clinically Applicable Skin Substitutes," Tissue Engineering Part C: Methods, vol. 18, No. 6, Jun. 1, 2012, pp. 464-471.
El-Sherbiny, I., et al. "Hydrogel scaffolds for tissue engineering; Progress and challenges" Global Cardiology Science & Practice 2013, vol. 2013, No. 3, Sep. 1, 2013, pp. 316-342.
United States Office Action, U.S. Appl. No. 19/026,572, filed Apr. 16, 2025, 9 pages.
United States Notice of Allowance, U.S. Appl. No. 19/026,572, filed Aug. 22, 2025, 7 pages.

* cited by examiner

*Primary Examiner* — Robert A Wax
*Assistant Examiner* — Kimberly Barber
(74) *Attorney, Agent, or Firm* — Fenwick & West LLP

(57) ABSTRACT

The invention relates to a fully disposable system for casting, polymerizing and compressing a hydrogel. The invention further relates to a method for producing a scaffold for the generation of artificial tissue products using said disposable system.

11 Claims, 11 Drawing Sheets

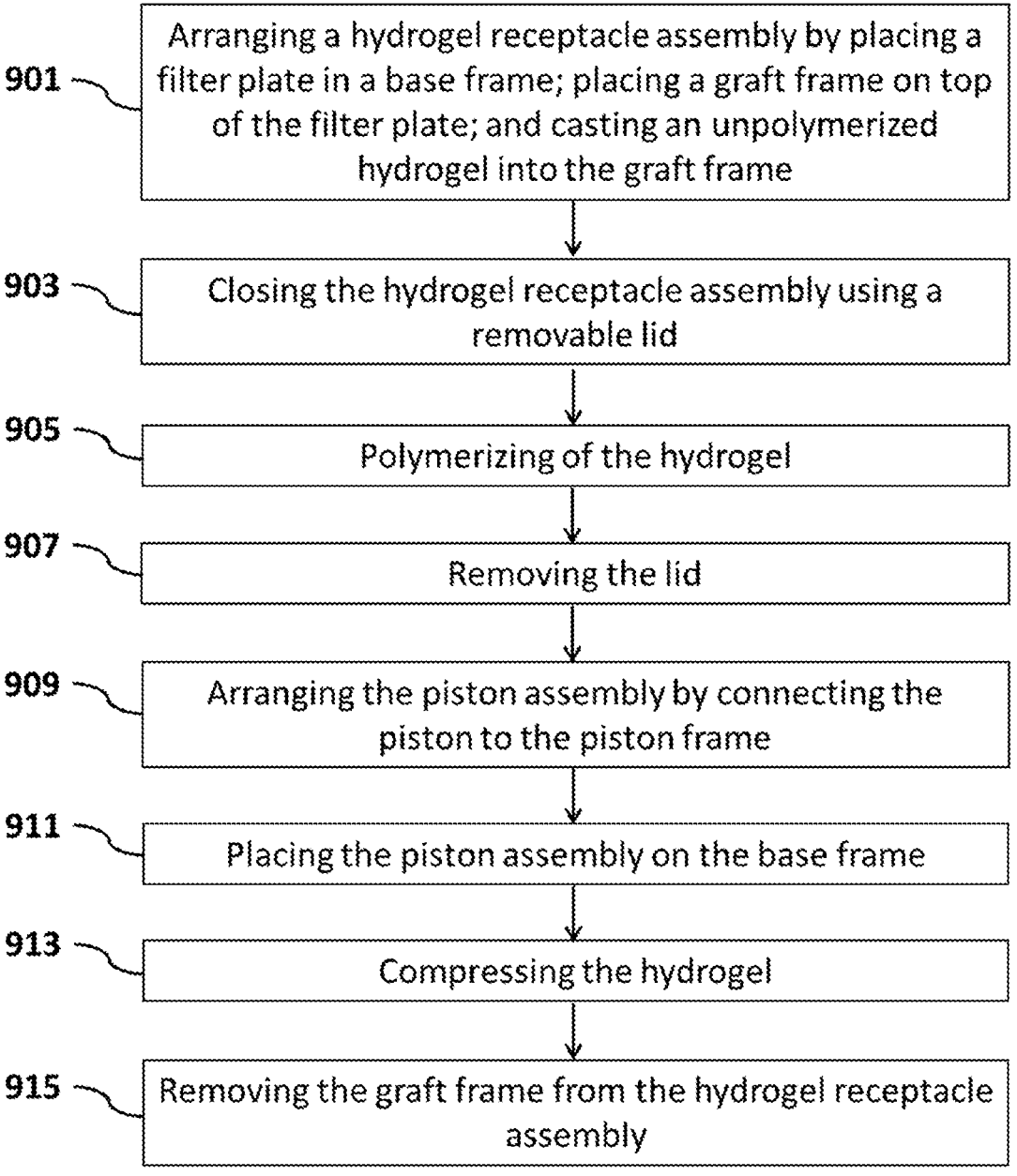

901 — Arranging a hydrogel receptacle assembly by placing a filter plate in a base frame; placing a graft frame on top of the filter plate; and casting an unpolymerized hydrogel into the graft frame 903 — Closing the hydrogel receptacle assembly using a removable lid 905 — Polymerizing of the hydrogel 907 — Removing the lid 909 — Arranging the piston assembly by connecting the piston to the piston frame 911 — Placing the piston assembly on the base frame 913 — Compressing the hydrogel 915 — Removing the graft frame from the hydrogel receptacle assembly

Fig. 1

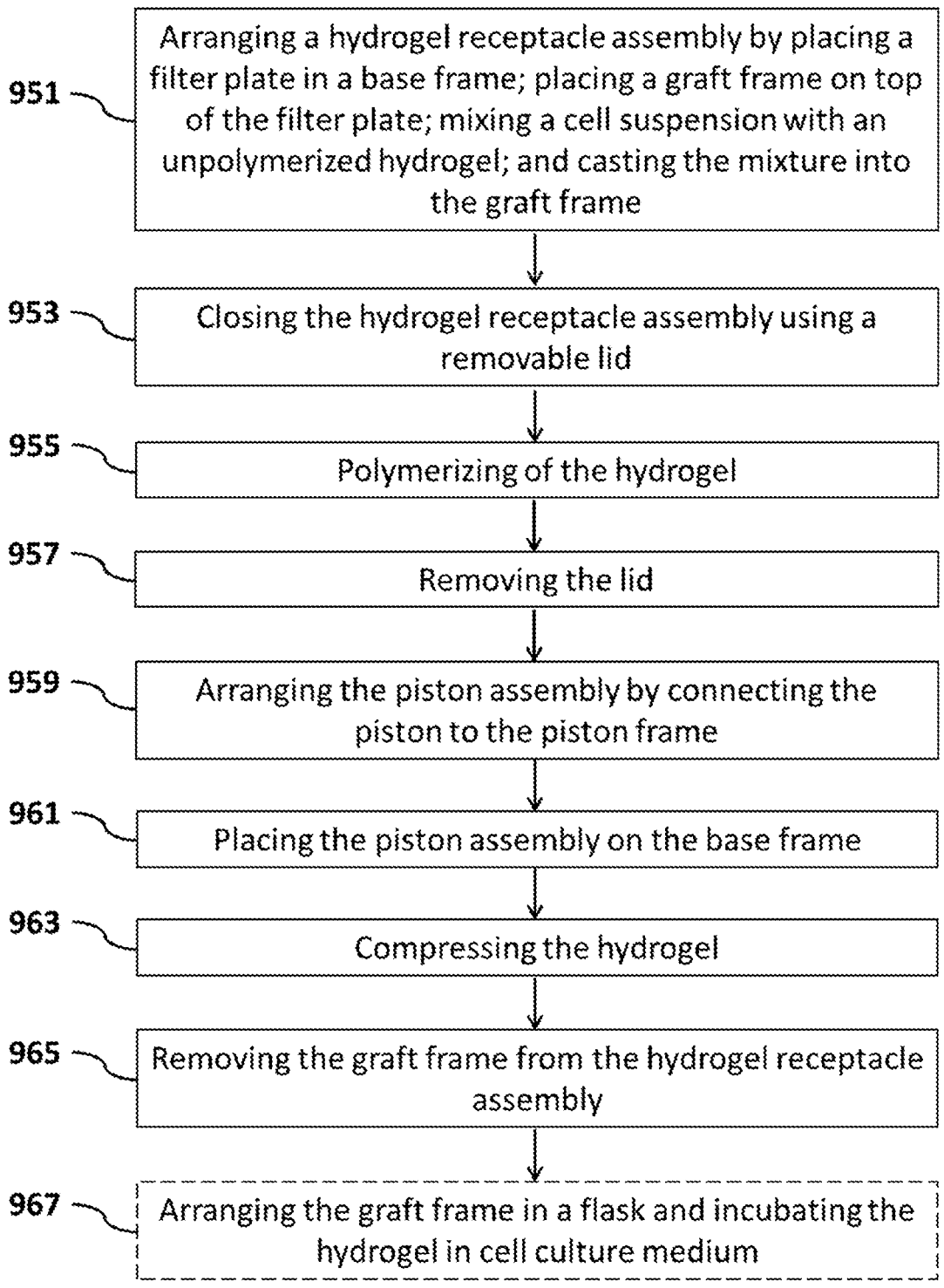

951 — Arranging a hydrogel receptacle assembly by placing a filter plate in a base frame; placing a graft frame on top of the filter plate; mixing a cell suspension with an unpolymerized hydrogel; and casting the mixture into the graft frame 953 — Closing the hydrogel receptacle assembly using a removable lid 955 — Polymerizing of the hydrogel 957 — Removing the lid 959 — Arranging the piston assembly by connecting the piston to the piston frame 961 — Placing the piston assembly on the base frame 963 — Compressing the hydrogel 965 — Removing the graft frame from the hydrogel receptacle assembly 967 — Arranging the graft frame in a flask and incubating the hydrogel in cell culture medium

Fig. 2

DISPOSABLE SYSTEM AND METHOD FOR PREPARING A COMPRESSED HYDROGEL

FIELD OF THE INVENTION

The present invention relates to a system for preparing a compressed hydrogel. More particularly, the invention relates to a fully disposable system for casting, polymerizing and compressing a hydrogel. The invention further relates to a method for producing a scaffold for the generation of an artificial tissue product using said disposable system.

BACKGROUND OF THE INVENTION

The extracellular matrix (ECM) in the human body is a three-dimensional network of extracellular macromolecules, such as collagen, enzymes, and glycoproteins, which provides structural and biochemical support for residing cells. In order to mimic the 3D-environment in a cell culture, for example, in the process of 3D tissue engineering, hydrogels are often used.

A hydrogel is a 3D network of natural or synthetic hydrophilic polymers that is able to absorb a large amount of water, while maintaining its structure, mainly due to chemical or physical cross-linking of individual polymer chains. Hydrogels can easily integrate living cells within the 3D matrix. For example, in order to produce a dermo-epidermal skin substitute, dermal fibroblasts are mixed with a collagen type I hydrogel, to which these cells readily attach (anchor) upon gelling of the hydrogel in three dimensions. These fibroblasts secrete necessary factors to the surrounding matrix, thereby providing a suitable micro-environment for subsequent keratinocytes attachment, proliferation and organization when these cells are added on the upper surface of the hydrogel.

Since a hydrogel has a flabby consistence, it can be mechanically compressed in order to increase its physical robustness, which then allows a surgeon to conveniently and securely handle the final gel/skin graft made from the compressed hydrogel and to apply it to the patient.

Some devices for compressing a hydrogel are known. However, various features of the known devices render the compression process relatively expensive, time consuming, prone to contamination, and having increased risk of damaging the graft.

It is therefore an object of the present invention to provide a system and a method for preparing a compressed hydrogel, which do not restrict production output in terms of costs, time and workflow, reduce potential for contamination and decrease the risk for damage to the final tissue product, thereby improving the quality and scalability of the produced tissue.

It is another object of the invention to provide a system and a method for producing a scaffold for the generation of artificial tissues.

Other objects and advantages of the invention will become apparent as the description proceeds.

SUMMARY OF THE INVENTION

The invention relates to a disposable system for preparing a compressed hydrogel, the system comprising:

(a) a hydrogel receptacle assembly, comprising:
  (i) a graft frame configured to accommodate a hydrogel layer; the graft frame comprising a circumferential frame member and a permeable membrane bottom connected to said frame member;

(ii) a porous filter plate; and (iii) a base frame, comprising a bottom wall; a circumferential wall extending from the bottom wall, so that the base frame forms a container that is configured to receive the filter plate and the graft frame in an operating mode, such that the filter plate is arranged between the bottom wall of the base frame and the membrane bottom of the graft frame; and a plurality of indentations located at one or more edges of the base frame;

(b) a removable lid; and (c) a piston assembly comprising:
  (i) a piston frame, comprising a frame member; a support structure extending from a first side of the frame member towards the membrane bottom in the operating mode; and a plurality of guiding extensions protruding from an edge of the frame member in the compression direction; the piston frame is configured to be slidably arranged on the base frame in the operating mode, such that each extension is associated to one of the indentations, so that the piston frame is guided by said extensions onto the base frame along the compression direction; and
  (ii) a piston configured to be connected to the piston frame in a releasable manner, such that in the operating mode the piston frame is configured to press the piston along the compression direction against the hydrogel layer residing in the graft frame so as to compress the hydrogel layer between the piston and the membrane bottom of the graft frame;

wherein the graft frame, the base frame, the filter plate, the lid, the piston and the piston frame are disposable.

In one embodiment, the base frame comprises one or more ledges providing support for the filter plate and/or the upper edge of the circumferential frame member of the graft frame.

In another embodiment, the base frame comprises an aperture for venting, which is covered with a filter that provides gas exchange while maintaining sterile conditions.

According to one embodiment of the invention, at least one side of the base frame comprises bulging joining elements, and at least one other side of the base frame comprises complementary slits that accommodate the joining elements of a second compression system.

According to another embodiment of the invention, the circumferential wall of the base frame comprises a plurality of drain channels to expel any overflowing liquid away from the hydrogel layer being compressed, over the upper edge of the graft frame and towards the base frame.

In one embodiment of the disposable system of the invention, the piston comprises a piston base designed to be inserted into the graft frame, such that a first side of the piston base forms a contact surface with the hydrogel layer during compression; and a circumferential edge region designed to contact the circumferential frame member of the graft frame when pressing against the hydrogel layer in a sealing manner.

The disposable system has a support structure of the piston frame which may comprise a support base, which forms a contact surface with the piston base, and a circumferential support wall connecting the support base to the frame member.

Furthermore, the disposable system may further comprise a flask for incubation of the compressed hydrogel layer, such that the flask is designed to receive the graft frame with the compressed hydrogel layer residing in said graft frame; wherein the flask comprises a top opening through which the graft frame can be arranged in an interior of the flask and a lid. The flask may be provided together with a support frame, which is designed to be arranged in said interior of the flask on a bottom of the flask and to provide a resting place for the graft frame inside the flask; wherein the lid is designed to seal said top opening of the flask.

Also encompassed by the invention is a method for preparing a compressed hydrogel, using the system according to an embodiment of the invention, the method comprising the steps of:

(a) arranging the hydrogel receptacle assembly, said arranging comprises:
  (i) placing the filter plate in the base frame;
  (ii) placing the graft frame in the base frame on top of the filter plate;
  (iii) casting an unpolymerized hydrogel into the graft frame so that said hydrogel forms a layer covering the membrane bottom of the graft frame;
(b) closing the hydrogel receptacle assembly using the removable lid;
(c) transferring the closed hydrogel receptacle assembly to an incubator for full polymerization of the hydrogel;
(d) transferring the closed hydrogel receptacle assembly back to a sterile environment (e.g., a workbench) and removing the lid;
(e) arranging the piston assembly by connecting the piston to the piston frame;
(f) placing the piston assembly on the base frame so that the guiding extensions of the piston frame are slidably arranged within the indentations of the base frame;
(g) compressing the hydrogel layer between the membrane bottom and the piston by applying a compression force to the second side of the frame member of the piston frame and letting the piston frame press with the piston along the compression direction against the hydrogel layer; and
(h) removing the graft frame from the system after having compressed the hydrogel layer and obtaining a compressed hydrogel.

In a further aspect, the present invention provides a method for producing a scaffold for the generation of an artificial tissue product using the system comprises the steps of:

(a) arranging the hydrogel receptacle assembly, said arranging comprises:
  (i) placing the filter plate in the base frame;
  (ii) placing the graft frame in the base frame on top of the filter plate;
  (iii) mixing a cell suspension with an unpolymerized hydrogel;
  (iv) casting the mixture of cells and unpolymerized hydrogel into the graft frame so that said hydrogel forms a layer covering the membrane bottom of the graft frame;
(b) closing the hydrogel receptacle assembly using the removable lid;
(c) transferring the closed hydrogel receptacle assembly to an incubator for full polymerization of the hydrogel;
(d) transferring the closed hydrogel receptacle assembly back to a sterile environment (e.g., a workbench) and removing the lid;
(e) arranging the piston assembly by connecting the piston to the piston frame;
(f) placing the piston assembly on the base frame so that the guiding extensions of the piston frame are slidably arranged within the indentations of the base frame;

(g) compressing the hydrogel layer between the membrane bottom and the piston by applying a compression force to the second side of the frame member of the piston frame and letting the piston frame press with the piston along the compression direction against the hydrogel layer;
(h) removing the graft frame from the system after having compressed the hydrogel layer; and optionally
(i) arranging the graft frame with the compressed hydrogel layer through a top opening of a flask into an interior of the flask on top of a support frame arranged on a bottom of the flask; closing the flask with a lid; and incubating the compressed hydrogel layer in cell culture medium so as to generate a graft from said compressed hydrogel layer; wherein the cell culture medium is added to the flask prior to arranging the graft frame into the interior of the flask, prior to closing the top opening of the flask with the lid, or after closing the top opening of the flask with the lid.

According to one embodiment of the invention, the artificial tissue product is an artificial skin graft, such that the cell suspension is a suspension of fibroblasts; wherein after having compressed the hydrogel layer, the compressed hydrogel residing in the graft frame is incubated in the flask until the fibroblasts have proliferated to biologically reasonable cell numbers; and wherein keratinocytes are added to the plane upper surface of the hydrogel, and the hydrogel is further incubated until the keratinocytes have formed a monolayer or stratified epithelium.

According to a specific embodiment of the invention, the unpolymerized hydrogel is an unpolymerized collagen hydrogel.

BRIEF DESCRIPTION OF THE DRAWINGS

In the drawings:

FIG. 1 shows steps in a method for preparing a compressed hydrogel using the system of the invention;

FIG. 2 shows steps in a method for producing a scaffold for the generation of an artificial tissue product using the system of the invention;

DETAILED DESCRIPTION OF THE INVENTION

Figure 3A:
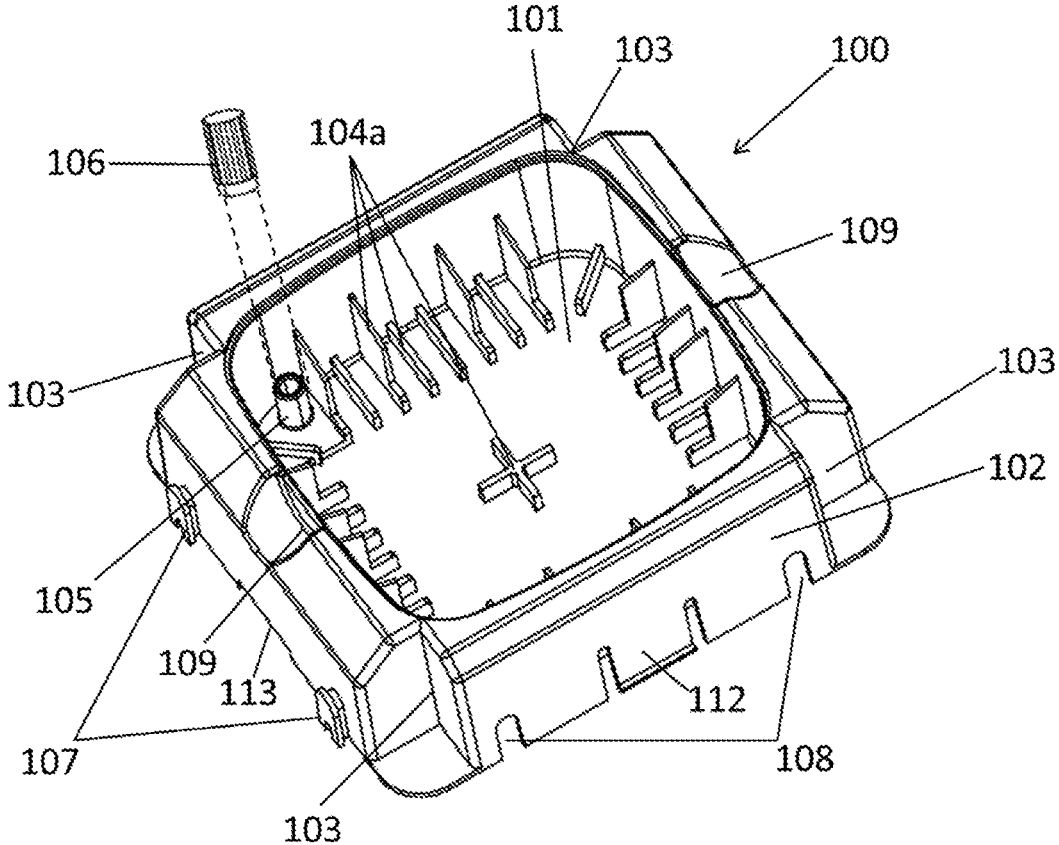
FIG. 3A shows a perspective view of the base frame (100) according to one embodiment of the invention.

Currently available devices for compressing a hydrogel possess various shortcomings in the graft production process. Particularly, these devices require cleaning and sterilization of the compression device prior to each use. By contrast, the device and system for preparing a compressed hydrogel according to the invention is fully disposable, and thus eliminates the re-sterilization and the corresponding validation requirements, as well as the potential for cross contamination between hydrogels. Therefore, the system disclosed herein reduces costs, as well as risks of contamination and damage to the produced graft, and increases production output.

The term "preparing a compressed hydrogel" as used herein refers to the process of casting, polymerizing and compressing a hydrogel. The process of preparing a compressed hydrogel can be used, for example, as part of the production of a tissue graft.

The term "disposable" as used herein refers to single-use items, i.e., items that are designed to be replaced after a single use.

The term "hydrogel" as used herein refers to a three-dimensional (3D) network of polymers that can hold a large amount of water while maintaining the structure due to chemical or physical cross-linking of individual polymer chains. The hydrogel can be used as a scaffold for supporting three-dimensional tissue formation. Polymers and materials suitable to be used as a scaffold for tissue engineering include, but are not limited to, polylactic acid (PLA), polyglycolic acid (PGA), polycaprolactone (PCL), derivatives of the extracellular matrix, protein materials (such as collagen or fibrin), polysaccharidic materials (such chitosan and glycosaminoglycans), decellularized tissue extracts (whereby the remaining cellular remnants/extracellular matrices act as the scaffold), and any combination thereof.

In one aspect, the present invention provides a disposable system for preparing a compressed hydrogel, the system comprising:

(a) a hydrogel receptacle assembly, comprising:
  (i) a graft frame configured to accommodate a hydrogel layer; the graft frame comprising a circumferential frame member and a permeable membrane bottom connected to said frame member;
  (ii) a porous filter plate; and
  (iii) a base frame (also sometimes referred to as "base tray"), comprising a bottom wall; a circumferential wall extending from the bottom wall, so that the base frame forms a container that is configured to receive the filter plate and the graft frame in an operating mode, such that the filter plate is arranged between the bottom wall of the base frame and the membrane bottom of the graft frame; and a plurality of indentations located at one or more edges of the base frame;

(b) a removable lid; and (c) a piston assembly comprising:
  (i) a piston frame (also sometimes referred to as "top plate" or "top tray"), comprising a frame member; a support structure extending from a first side of the frame member towards the membrane bottom in the operating mode; and a plurality of guiding extensions protruding from an edge of the frame member in the compression direction; the piston frame is configured to be slidably arranged on the base frame in the operating mode, such that each extension is associated to one of the indentations, so that the piston frame is guided by said extensions onto the base frame along the compression direction; and
  (ii) a piston (also sometimes referred to as "piston plate") configured to be connected to the piston frame in a releasable manner, such that in the operating mode the piston frame is configured to press the piston along the compression direction against the hydrogel layer residing in the graft frame so as to compress the hydrogel layer between the piston and the membrane bottom of the graft frame;

wherein the graft frame, the base frame, the filter plate, the lid, the piston and the piston frame are disposable.

As can be appreciated, all the components of the system that come in contact with the hydrogel or the solutions/liquids contained within the system, namely, all the components listed above are disposable. This feature of the system disclosed herein prevents the need to manufacture the components to be durable for continuous long-term use, for example, components made of heavy steel or expensive polymers. Instead, the disposable components can be made of lighter weight and regular medical grade and biocompatible materials. Accordingly, a system comprising all disposable components enables easier operator workflow at a lower cost per graft.

According to a specific embodiment of the invention, the base frame (or tray), the graft frame (with the exception of the membrane bottom) and the piston frame are made of polyether ether ketone (PEEK). According to another specific embodiment, the piston is made of polypropylene. According to a further specific embodiment, the base frame, the graft frame, the piston frame and the piston plate are made of polycarbonate (PC), polystyrene (PS) and/or methyl methacrylate-acrylonitrile-butadiene-styrene (MABS).

According to the system disclosed herein, the hydrogel receptacle assembly and the removable lid form a hydrogel polymerization assembly, such that the hydrogel (in a liquid form) is poured into the graft frame, which is placed in the base frame, on top of the filter plate. The hydrogel receptacle assembly is then closed with the removable lid and the entire closed hydrogel polymerization assembly can be transferred to a suitable incubator for gelification, while remaining sterile. It should be noted that the hydrogel polymerization assembly that is closed with the removable lid is air-tightly sealed in order to avoid contamination of the hydrogel. Afterwards, the hydrogel polymerization assembly is taken out of the incubator and placed in a sterile environment, where the lid is removed and the piston assembly is placed on the base frame (still containing the filter plate and the graft frame now carrying the polymerized hydrogel) to form a compression assembly. Compression is carried out by applying a compression force to the compression assembly along the compression direction.

According to some embodiments of the invention, the base frame comprises one or more ledges providing support for the other parts of the system. According to one embodiment the base frame comprises a ledge on which the filter plate rests and/or a ledge, on which an upper edge of the circumferential frame member of the graft frame rests. In another embodiment, the base frame comprises additional ledges providing support for additional components of the system of the invention, such as the piston frame.

According to a specific embodiment of the invention, the ledge comprises at least one single circumferential step on the circumferential wall of the base frame. According to another specific embodiment, the ledge comprises a plurality of steps, such that each step of the plurality of steps can provide support to at least one of the components of the systems. For example, some steps of the plurality of steps are designed to provide support solely to the filter plate, while other steps of the plurality of steps are designed to provide support for both the filter plate and the circumferential frame member of the graft frame. The steps may be positioned immediately adjacent to the circumferential wall of the base frame, separately from said circumferential wall or at the center of the base frame. According to a further specific embodiment, the ledge comprises a combination of the circumferential step and steps. For example, the ledge may comprise a circumferential step, as well as a step at the center of the base frame.

As would be appreciated by a skilled artisan, the shape of the plurality of steps may vary according to the specific components of the system of the invention for which the steps provide support. In a non-limiting example, steps providing support solely to the filter plate may be shaped as a rectangular, square or a "plus" sign ("+"), while the steps providing support for both the filter plate and the upper edge of the circumferential frame member may be shaped as the letter "L".

According to yet another specific embodiment of the invention, the circumferential step comprises at least one recess for receiving a region of the frame member of the graft frame in a form-fitting manner in order to prevent any unintentional movement of the graft frame resting within the base frame during compression. Alternatively, the region of the frame member and the plurality of steps may be designed such that said region fits snugly between two or more of the plurality of steps.

In some embodiments, the base frame comprises two or more circumferential steps that provide support to the edges of other components of the system, for example, the graft frame and/or the piston frame.

According to one embodiment of the invention, the base frame also comprises an aperture for venting purposes, particularly, to prevent accumulation of $CO_2$ within the system during incubation periods and thus avoid any consequent changes in the pH of solutions (e.g., culture medium) contained in the system, which in turn may affect the polymerization of the hydrogel, as well as potentially be harmful to the cells grown within the hydrogel scaffold. In order to avoid contamination of the solutions and cells grown within the hydrogel scaffold, the aperture is covered with a filter suitable to provide gas exchange while maintaining sterile conditions and prevent pressure buildup during compression. The aperture and covering filter may either be cylindrical in shape or in form of a flat disc, bonded to the underside of the base tray in a molded recess. According to a specific embodiment the filter is made of a sintered polymer. Non-limiting examples of suitable filters to be used in the system described herein include the commercially available Porex INTAKE™ Reagent Filter and OxyPad® (by Oxyphen).

According to another embodiment, at least one side of the base frame comprises bulging joining elements, and at least one other side of the base frame comprises complementary slits that accommodate the joining elements of a second compression system, thus providing linkage between at least two compression systems. The linkage between a plurality of compression systems enables simultaneous handling of the plurality of systems, for example, simultaneous transfer of the plurality of systems in or out of an incubator. It should be noted that the shape, size, and number of the bulging joining elements and complementary slits may vary, as long as the linkage between the plurality of systems cannot be easily disrupted by unintentional movement of one linked system compared to the other linked system.

According to a further embodiment, at least one side of the base frame comprises on or more hooks, and at least one other side of the base frame comprises one or more complementary niches that accommodated the hooks of a second compression system, thus providing linkage between at least two compression systems in a "snap-lock" mechanism. This means that the hook is briefly deflected during the linkage operation and catches in the corresponding niche of a mating compression system. After the linkage operation, the hook returns to a stress-free condition so as to prevent unintentional movement of one linked system compared to the other linked system.

In a specific embodiment of the invention, at least two compression systems may be linked by both the bulging joining elements and corresponding slits mechanism and the hook and corresponding niche mechanism as described above.

According to yet another embodiment, the upper edge of the circumferential wall of the base frame comprises at least one recess that provides excess for a user to easily remove components residing in the base frame (i.e. the graft frame, the lid and the piston) from the interior of the base frame, e.g. manually or by means of a tool, e.g. forceps.

In some embodiments, the base frame also comprises an extended lip that protrudes from the upper edge of the circumferential wall at a plane parallel to that of the bottom wall of the base frame and then turns downwards. The extended lip supports the stability of the base frame, and provides a possible resting place for the piston frame. Accordingly, the bulging joining elements and complementary slits are located on the extended lip instead of the circumferential wall of the base frame.

According to other embodiments, the circumferential wall of the base frame comprises a plurality of drain channels that expel any overflowing liquid away from the hydrogel layer being compressed, over the upper edge of the graft frame and towards the base frame.

According to the present invention, the filter plate is arranged in the base frame such that an outer circumferential edge of the filter plate rests on a plurality of steps or on a single circumferential step located in the base frame. The filter plate consists of a porous material designed to "trap" the liquids that are compressed out of the hydrogel layer. Furthermore, the porous filter plate also provides a vertical support and stability, which is needed during the compression order to maintain a uniform graft thickness.

According to one embodiment of the invention, the circumferential frame member of the graft frame comprises an upper edge protruding from the area of the circumferential frame member. The upper edge provides an anchor for the graft frame to rest upon corresponding ledges or edges of other components of the system as further described herein.

As would be appreciated by a person skilled in the art, the membrane bottom of graft frame is permeable to water, such that water-based liquids can be squeezed out of the hydrogel layer during compression. In addition, the permeable membrane bottom allows liquids, such as cell culture medium, to come in contact with the hydrogel layer from both underneath and above the hydrogel layer.

According to one embodiment of the invention, the membrane bottom consists of polyethylene terephthalate (PET). According to a specific embodiment, the membrane bottom is 18 micrometers thick. According to another specific embodiment the membrane bottom has a pore-diameter of 3 micrometers.

In a non-limiting example, RoTrac® Track-Etched Membranes (by Oxyphen) are suitable for use as the member bottom in the compression device described herein.

According to a specific embodiment, the membrane bottom has an area of 7 cm×8 cm, however, other sizes are also possible.

According to some embodiments, the membrane bottom is integrally connected to the frame member.

According to the system described herein, upon compression of the hydrogel layer, liquid is pressed out of the hydrogel and flows through the membrane bottom of the graft frame and the filter plate into the base frame, where the liquid accumulates on the bottom of the base frame. In some embodiments of the invention, liquid flowing over the upper edge of the graft frame is also directed into the base frame via a plurality of drain channels (also termed herein "overflow channels").

The removable lid is designed to hermetically seal the hydrogel receptacle assembly of the system, so as to prevent any unfiltered exchange of liquids or gas between the interior and exterior of the system. Thus, the lid ensures that the graft remains sterile even when the system is transferred out of a sterile environment, for example, transferred out of the sterile workbench into an incubator and back. According to one embodiment of the invention, the lid comprises a circumferential gasket that contributes to the sealing function of the lid. In another embodiment of the invention, the lid comprises at least one gripping element that facilitates easy gripping of the lid by a user from the exterior of the system, and subsequently removal of the lid from the hydrogel receptacle assembly of the system. In a non-limiting example, the lid is a re-closable lid supplied with commercially available tissue culture flasks (such as TPP® flasks with re-closable lid).

The piston (or piston plate), according to the system described herein, comprises a piston base, such as a plate-like piston base, which is designed to be inserted into the graft frame, such that a first side of the piston base forms a contact surface with the hydrogel layer during compression. The piston base also comprises a circumferential edge region designed to contact the circumferential frame member of the graft frame when pressing against the hydrogel layer in a sealing manner. The sealing contact between the circumferential edge region of the piston and the circumferential frame member of the graft frame reduces the flow of liquid during compression over the circumferential frame member, such that most of the liquid is expelled from the hydrogel through the bottom membrane and absorbed by the filter plate. In addition, the sealing contact prevents any liquid flowing out over the circumferential frame member from returning to the interior of the graft frame. Moreover, said sealing contact prevents the hydrogel layer from getting past the circumferential edge region of the piston, thus forcing the hydrogel layer to fully remain within the graft frame.

According to one embodiment, the piston comprises at least two latching elements protruding from an edge region on a second side of the piston base facing away from said first side. The latching elements enable an easy fastening of the piston to the support structure of the piston frame, as well as easy releasing of the piston from the support structure, by disengaging of the piston from the support structure. Accordingly, said latching elements are designed to be associated with corresponding apertures on the support structure of the piston frame, for releasably connecting the piston to the piston frame. Accordingly, when the latching elements are engaged with the said apertures, the latching elements are accessible, e.g. manually or by means of a tool, from a second side of the piston frame facing away from the membrane bottom. This access enables the release of the latching elements from the support structure through said apertures, for example, by bending them away from the support structure, in order to bring them out of engagement with the support structure.

According to a specific embodiment, the edge region comprises two latching elements positioned directly opposite from one another.

As should be appreciated by a skilled artisan, the shape and size of the latching elements may vary, as long as the fastening of the piston to the support structure of the piston frame cannot be released by simply sliding the piston frame away from the piston, but requires an application of an external force, either manually or by means of a tool, to disengage.

According to another embodiment of the invention, the piston comprises guiding elements protruding from the edge region of the piston base on said second side of the piston base, said guiding elements are designed to slide along said support base for guiding the piston with respect to the support structure when the piston is connected to the support structure.

It should be noted that the number and shape of the guiding elements may vary according to the size and shape of the piston base.

According to the system described herein, at the first side of the frame member, the support structure holds the piston.

According to some embodiments of the invention, the support structure of the piston frame (or top plate) comprises a support base, which forms a contact surface with the piston base, and a circumferential support wall connecting the support base to the frame member. In one embodiment of the invention, the circumferential support wall is positioned vertically, namely, perpendicular to the plane of the support base. In another embodiment, the support wall is positioned diagonally at an angle suitable to connect the support base with an inner margin of the frame member, where the dimensions of said support base are smaller than the dimensions of said inner margin of the frame member.

In yet another embodiment, the support structure is designed such that the compression of the hydrogel (between the piston and the membrane bottom) has a pre-defined thickness, for example, a thickness of 1 mm. A pre-defined thickness of the hydrogel can be achieved by specific dimensions of components of the piston assembly. Alternatively, the thickness of the compressed hydrogel can be defined by spacer components, for example, a spacer located between the piston frame and the piston plate.

In a specific embodiment of the invention, the support structure is further connected to the frame member at the first side of said frame member by stabilizing elements, in order to prevent any unintentional and undesired movement of the support structure during compression. It should be noted that the number and shape of the stabilizing elements may vary according to the sizes and shapes of the support wall and frame member.

According to the system described herein, a compression force is applied to the second side of the frame member of the piston frame, such that the piston frame is pressed with the piston along the compression direction against the hydrogel layer. In one embodiment of the invention, said compression force can be applied by placing one or more compression weights at the second side of the frame member of the piston frame. Accordingly, at the second side of the frame member the support structure forms a receptacle for accommodating the one or more compression weights, such that the one or more compression weights apply said compression force to the piston frame in the compression direction, which in turn applies force to the piston and consequently to the hydrogel layer residing in the graft frame. According to a specific embodiment, the piston frame comprises stabilizing elements at the second side of the frame member that prevent any unintentional and undesired movement of the support structure during compression, as well as prevent any unintentional and undesired movement of the one or more compression weights. It should be noted that the number and shape of the stabilizing elements may vary, as long as they ensure that the one or more compression weights are stacked on the center of the support base.

As would be appreciated by a skilled artisan, the magnitude of the compression force applied to the piston frame is adjusted by the number of compression weights stacked in the receptacle on the second side of the piston frame, which is designed to accommodate the compression weights. The magnitude of the force can also be adjusted by using compression weights having different masses, as desired by the operator of the system.

Alternatively, the compression force can be applied by other means, e.g., by a force/displacement controlled uniaxial compression machine.

It should be noted that the timing of the compression process, as well as any combination of timing and force magnitude, can be defined by the operator of the system.

According to some embodiments of the present invention, the system described herein further comprises a flask for incubation of the compressed hydrogel layer, such that the flask is designed to receive the graft frame with the compressed hydrogel layer residing in said graft frame.

According to one embodiment, the flask comprises a top opening through which the graft frame can be arranged in an interior of the flask. For closing and sealing said top opening properly in order to maintain sterile conditions within the flask, a lid of the flask is provided.

According to another embodiment, the flask is provided together with a support frame, which is designed to be arranged in said interior of the flask on a bottom of the flask and to provide a resting place for the graft frame inside the flask. In a specific embodiment, the lid is designed to press the graft frame against the support frame when the lid closes said top opening of the flask. According to another specific embodiment, a transport grid may be provided, which is designed to be arranged between the graft frame and the lid, wherein the lid presses against said transport grid and the transport grid in turn presses against the graft frame, which is then pressed against the support frame when the lid closes the opening of the flask. The pressing of the graft frame against the support frame when the lid closes the top opening of the flask prevents random or unintentional movement of the graft frame in the interior of the flask and thus prevents the graft from any damages during transport.

According to another embodiment, the flask comprises a further opening for gas exchanges and optionally for handling (i.e., filling in, or sucking off) a liquid, for example, a cell culture medium, wherein a screw cap (optionally, with a filter membrane for gas exchange) is provided for closing said further opening.

In a specific embodiment, the flask is transparent at least in one section, for example, the top section, to enable visual inspection of the hydrogel (or cells) from the exterior of the flask and without extracting the graft frame containing the hydrogel from the interior of the flask.

According to yet another embodiment, the flask and/or the support frame are disposable.

According to a further embodiment of the invention, the support frame comprises recesses formed in an upper edge of the support frame for receiving the region of the circumferential frame member of the graft frame, wherein the graft frame is designed to rest with its upper edge on said upper edge of the support frame. According to yet a further embodiment of the invention, when the graft frame is placed upon the support frame inside the flask, a gap is maintained between the membrane of the graft frame and the bottom of the flask, such that the membrane is in full and uniform contact with the liquid (e.g., cell culture medium) present in the flask, in order to allow effective fluid exchange between the liquid and the bottom of the hydrogel layer. According to a specific embodiment, the support frame rests with four stands on said bottom of the flask. According to another specific embodiment, the support frame comprises two opposing protruding regions for contacting a wall of the flask from the interior of the flask so that the support frame cannot be displaced inside the flask in a lateral direction.

According to one embodiment of the invention, the hydrogel layer is used for generating an artificial skin graft that can be grafted onto a patient. Particularly, the hydrogel contains autologous human dermal fibroblasts, while autologous human epidermal keratinocytes are situated on the hydrogel, i.e., at an upper surface of the hydrogel layer facing away from the membrane bottom on which the hydrogel resides, and develops into a monolayer or stratified squamous epithelial surface (epidermis). According to a specific embodiment, the hydrogel consists of medical grade bovine collagen type I.

In another aspect, the present invention provides a method for preparing a compressed hydrogel, using the system disclosed above, as set forth in FIG. 1 the method comprising the steps of:

(a) arranging the hydrogel receptacle assembly (step 901 in FIG. 1), said arranging comprises:
        (i) placing the filter plate in the base frame;
        (ii) placing the graft frame in the base frame on top of the filter plate;
        (iii) casting an unpolymerized hydrogel into the graft frame so that said hydrogel forms a layer covering the membrane bottom of the graft frame;
    (b) closing the hydrogel receptacle assembly using the removable lid (step 903 in FIG. 1);
    (c) transferring the closed hydrogel receptacle assembly to an incubator for full polymerization of the hydrogel (step 905 in FIG. 1);
    (d) transferring the closed hydrogel receptacle assembly back to a sterile environment (e.g., a workbench) and removing the lid (step 907 in FIG. 1);
    (e) arranging the piston assembly by connecting the piston to the piston frame (step 909 in FIG. 1);
    (f) placing the piston assembly on the base frame so that the guiding extensions of the piston frame are slidably arranged within the indentations of the base frame (step 911 in FIG. 1);
    (g) compressing the hydrogel layer between the membrane bottom and the piston by applying a compression force to the second side of the frame member of the piston frame and letting the piston frame press with the piston along the compression direction against the hydrogel layer (step 913 in FIG. 1); and (h) removing the graft frame from the system after having compressed the hydrogel layer and obtaining a compressed hydrogel (step 915 in FIG. 1).

According to one embodiment of the invention, the incubator in step (c) is set at 37° C. According to a specific embodiment, the closed hydrogel receptacle assembly is incubated for at least 30 minutes at 37° C.

According to another embodiment, the step of removing the graft frame from the system is carried out by first releasing the piston frame from the piston, for example, by disengaging the latching elements connecting between the two components. After removing the piston frame from the piston, the graft frame is removed from the base frame while the piston is still in contact with the hydrogel residing within the graft frame, for example, by accessing the graft frame through the recesses provided in upper edge of the circumferential wall of the base frame. Then, the piston is carefully lifted from the hydrogel. It should be noted that the piston can also be removed together with the piston frame; however, since the piston tends to stick to the hydrogel layer, it is recommended to first remove the piston frame and then remove the piston, as described above, so as to reduce the risk of damaging the hydrogel.

In some embodiments the compressed hydrogel obtained by the method described above is used as a scaffold in the generation of artificial tissues.

Accordingly, the method for preparing a compressed hydrogel described above is adapted to a method for producing a scaffold for an artificial tissue product by mixing a cell suspension with the unpolymerized hydrogel prior to the casting of said unpolymerized hydrogel into the graft frame. In addition, the method for producing a scaffold for an artificial tissue product optionally comprises further incubation of the compressed hydrogel by arranging the graft frame with the compressed hydrogel layer through a top opening of a flask into an interior of the flask on top of a support frame arranged on a bottom of the flask; closing the flask with a lid; and incubating the compressed hydrogel layer so as to generate a graft from said compressed hydrogel layer.

In view of the above, the present invention also encompasses a method for producing a scaffold for the generation of an artificial tissue using the system of the invention, as set forth in FIG. 2, the method comprising the steps of:

(a) arranging the hydrogel receptacle assembly (step 951 in FIG. 2), said arranging comprises:
  (i) placing the filter plate in the base frame;
  (ii) placing the graft frame in the base frame on top of the filter plate;
  (iii) mixing a cell suspension with an unpolymerized hydrogel;
  (iv) casting the mixture of cells and unpolymerized hydrogel into the graft frame so that said hydrogel forms a layer covering the membrane bottom of the graft frame;

(b) closing the hydrogel receptacle assembly using the removable lid (step 953 in FIG. 2);

(c) transferring the closed hydrogel receptacle assembly to an incubator for full polymerization of the hydrogel (step 955 in FIG. 2);

(d) transferring the closed hydrogel receptacle assembly back to a sterile environment (e.g., a workbench) and removing the lid (step 957 in FIG. 2);

(e) arranging the piston assembly by connecting the piston to the piston frame (step 959 in FIG. 2);

(f) placing the piston assembly on the base frame so that the guiding extensions of the piston frame are slidably arranged within the indentations of the base frame (step 961 in FIG. 2);

(g) compressing the hydrogel layer between the membrane bottom and the piston by applying a compression force to the second side of the frame member of the piston frame and letting the piston frame press with the piston along the compression direction against the hydrogel layer (step 963 in FIG. 2);

(h) removing the graft frame from the system after having compressed the hydrogel layer (step 965 in FIG. 2); and optionally (as indicated by the dashed line in FIG. 2)

(i) arranging the graft frame with the compressed hydrogel layer through a top opening of a flask into an interior of the flask on top of a support frame arranged on a bottom of the flask; closing the flask with a lid; and incubating the compressed hydrogel layer in cell culture medium so as to generate a graft from said compressed hydrogel layer; wherein the cell culture medium is added to the flask prior to arranging the graft frame into the interior of the flask, prior to closing the top opening of the flask with the lid, or after closing the top opening of the flask with the lid (step 967 in FIG. 2).

According to one embodiment, the compressed hydrogel layer, which is placed in the graft frame and arranged in the interior of the flask (on top of the support frame), is incubated in a liquid suitable for maintaining the viability of cells and/or promoting cell growth, for example, saline, phosphate-buffered saline, or cell culture medium. Said liquid can be provided to the flask through the top opening or the further opening of the flask. It should be noted that the liquid can be added to the flask prior to arranging the graft frame into the interior of the flask, prior to closing the top opening with the lid, or after closing the top opening with the lid (in the latter case, the liquid is provided through the further opening of the flask). Prior to placing the flask in a suitable incubator, the flask should be in a closed state, such that the top opening is covered by the lid and the further opening is covered by a screw cap.

The production of scaffolds for the generation of various tissues using the system of the invention is also encompassed by the present invention. Naturally, the type of tissue product is dependent on the source tissue from which the cells to be mixed with the unpolymerized hydrogel are derived.

In one embodiment of the invention, the cells used in the method described above are animal or human autologous and/or allogeneic fibroblasts that were isolated from tissues including, but not limited to, dermis, tendon, lung, umbilical cord, cartilage, urethra, corneal stroma, oral mucosa, and intestine. In addition, said fibroblasts can be isolated by microdissection from the dermal papilla of hair follicles. In another embodiment of the invention, various cell types, other than fibroblasts, may be used, and these include, but are not limited to, epithelial cells, corneal stroma cells, smooth muscle cells, chondrocytes and other connective tissue cells of mesenchymal origin.

The animal-originated or human autologous and/or allogeneic epithelial cells can be derived from a number of source tissues including, but not limited to, epidermis, skin, lung, umbilical cord, urethra, corneal stroma, oral mucosa, intestine, bladder, esophagus, and cornea.

As mentioned above, the cells to be used in the method of the invention can be human cells or animal-derived cells. Such animal-originated cells can be derived, for example, from mammal species including, but not limited to, equine, canine, porcine, bovine, and ovine; or from rodent species, such as mouse or rat.

It should also be noted that cell donors may vary in developmental stage and age. Accordingly, cells may be derived from donor tissues of embryos, neonates, or older individuals including adults. In a non-limiting example, embryonic progenitor cells, such as mesenchymal stem cells, may be used to produce a scaffold according to the invention. The progenitor cells can be induced to differentiate into various types of tissues.

Moreover, cells that are spontaneously, chemically or virally transfected, or recombinant cells, or otherwise genetically engineered cells, such as induced pluripotent stem cells, may also be used in the method of the invention.

In addition, mixtures or chimeric mixtures of natural cells derived from two or more sources; or mixtures of natural and genetically modified or transfected cells; or mixtures of cells of two or more species or tissue sources may be used, to generate a tissue product that incorporates two or more cell types.

The hydrogel to be compressed by the system of the invention and used in the scaffold for generating tissue products can be any natural or synthetic extracellular matrix or hydrogel that are biocompatible. Non-limiting examples of such matrices and hydrogels include collagen, fibrin, fibrinogen, laminin, glycosaminoglycans (GAGs), gelatin, alginate, and any combination thereof.

In some embodiments of the invention, the artificial tissue product is a tissue graft or a hydrogel patch. The tissue product can be used for various applications, such as tissue replacement and tissue regeneration.

According to one embodiment of the invention, the artificial tissue product is an artificial skin graft, such that the cell suspension to be mixed with the unpolymerized hydrogel is a suspension containing animal-originated or human autologous and/or allogeneic dermal fibroblasts. According to a specific embodiment of the invention, the fibroblasts are autologous human dermal fibroblasts.

According to another embodiment of the invention, the hydrogel layer to be compressed in the method described herein is a collagen-based hydrogel. In a specific embodiment, the collagen hydrogel is prepared by dissolving collagen monomers (for example, collagen type I) in an acidic solution (thus rendering the quasi-liquid unpolymerized gel less viscous and easier to handle). Then, the cell suspension comprising dermal fibroblasts in a pH-buffered solution is added, thereby neutralizing the acidic pH of the gel. The mixture of the cells and collagen monomers is then rapidly cast into the graft frame residing in the hydrogel receptacle assembly described above.

According to a further embodiment of the invention, in order to produce a skin product ready to be grafted, the hydrogel containing the fibroblasts, after being compressed, is incubated until the fibroblasts have proliferated to biologically reasonable cell numbers. Thereafter, keratinocytes are added to the plane upper surface of the gel, and the gel is further incubated until the keratinocytes have formed a monolayer or stratified epithelium (i.e., an epidermis layer). Similar to fibroblasts, the keratinocytes may also be derived from animal or human autologous and/or allogeneic dermis.

According to a specific embodiment, the compressed hydrogel containing the fibroblasts is incubated for 5-10 days, and the gel containing the fibroblasts and the keratinocytes is further incubated for 5-10 days. Thus, after 10-20 days the "hydrogel", which has turned into a dermo-epidermal skin graft can be transplanted onto the patient.

It should be noted that other type of cells naturally residing in skin tissue can be added to the artificial skin graft. Non-limiting examples of such cells include mesenchymal stem cells (MSCs), vascular endothelial cells (for facilitating vascularization) and melanocytes (for pigmentation). Other cells naturally residing in the dermis layer or epidermis layer of the skin are also included.

Reference will now be made to several detailed embodiments of the present invention, examples of which are illustrated in the accompanying figures. Wherever practicable, similar or like reference numbers may be used in the figures and may indicate similar or like functionality. The figures depict embodiments of the present invention for purposes of illustration only. One skilled in the art will readily recognize from the following description that alternative embodiments of the structures illustrated herein may be employed without departing from the principles of the invention described herein.

FIGS. 3 to 7 show a system for preparing a compressed hydrogel H, comprising a hydrogel receptacle assembly, a lid, a piston assembly and one or more compression weights. The piston assembly comprises a piston (500) and a piston frame (600). The hydrogel receptacle assembly, in which the polymerization of the hydrogel takes place, comprises a base frame (100) being designed for holding/guiding a filter plate (200), a graft frame (300) containing a hydrogel layer (H) and a removable lid (400). After gelification, the lid (400) is removed and the piston assembly is placed on the hydrogel receptacle assembly for compression, such that the piston frame (600) presses the piston (500) along a compression direction (C) against a hydrogel layer (H) arranged in the graft frame 300 positioned in the base frame (100).

FIG. 3A shows a perspective view of the base frame (100) according to one embodiment of the invention. The base frame (100) comprises a bottom wall (101), a circumferential wall (102) protruding from the bottom wall (101), a plurality of indentations (103) located at the corners of the base frame (100), a plurality of steps (104a) to provide support for the other components of the system. The base frame (100) also comprises an aperture (105) for venting purposes, said aperture (105) is covered with a filter (106) suitable to provide gas exchange under sterile conditions and prevent pressure buildup during compression. Furthermore, at least one side of the base frame (100) shown in FIG. 3A comprises bulging joining elements (107) and at least one other side of the base frame (100) comprises complementary slits (108) that accommodate the bulging joining elements of a second compression system. In addition, at least one side of the base frame (100) shown in FIG. 3A comprises a hook (112) and at least one other side of the base frame (100) comprises a complementary niche (113) that accommodate the hook of a second compression system. The upper edge of the circumferential wall (102) comprises two recesses (109) on opposite sides of the circumferential wall that enable easy removal of components residing in the base frame (i.e. the graft frame, the lid and the piston) from the interior of the base frame (100).

Figure 3B:
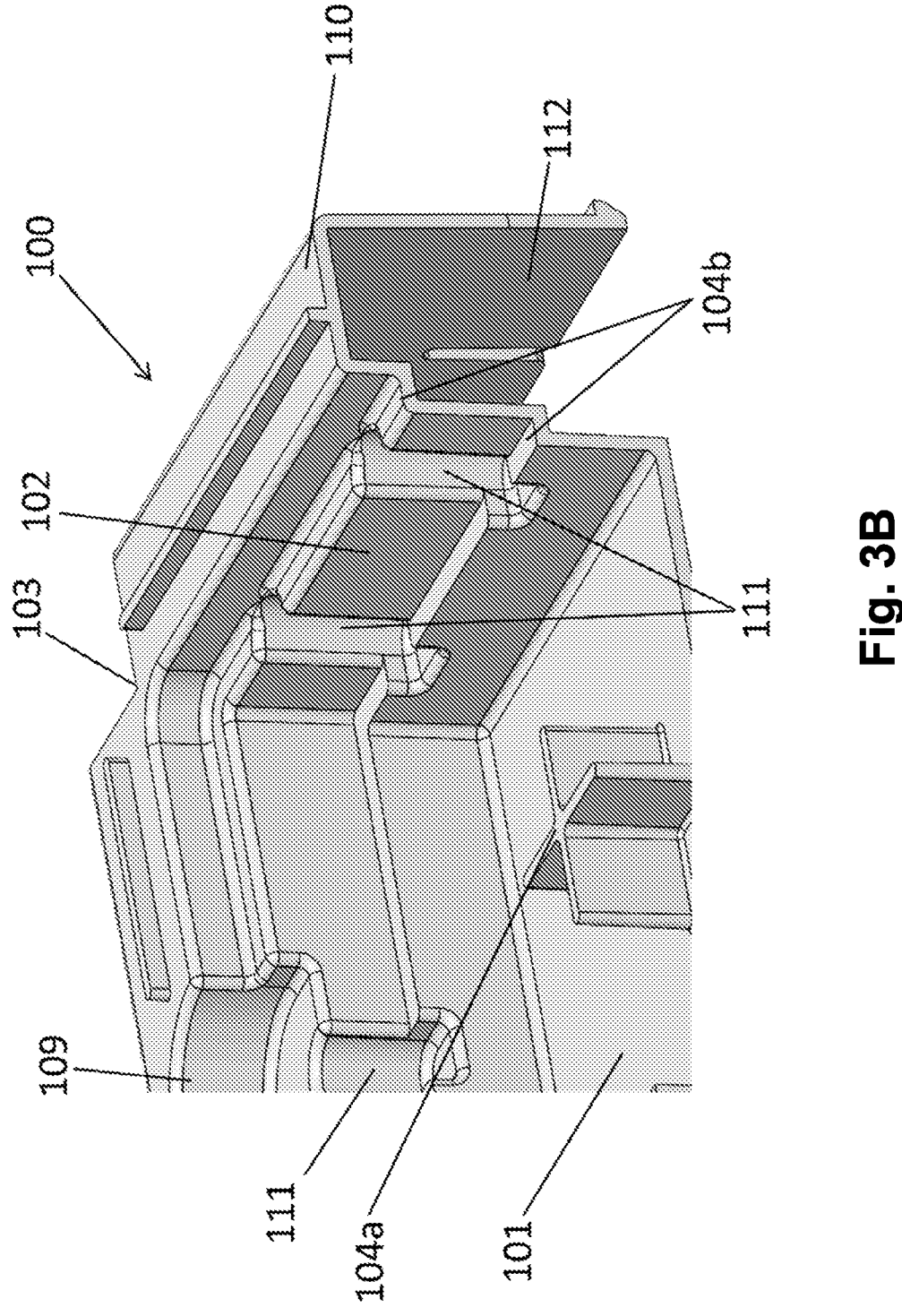
FIG. 3B shows a perspective view of a one corner of a cross-sectioned base frame (100) according to one embodiment of the invention.

FIG. 3B shows a perspective view of a one corner of a cross-sectioned base frame (100) according to a different embodiment of the invention, in which instead of the plurality of steps (104a) of FIG. 3A, a single step is included in the circumferential wall (102) of the base frame (100). Thus, the presented corner of base frame (100) shown in FIG. 3B comprises a bottom wall (101), a circumferential wall (102), one of the plurality of indentations (103), a center step (104a) and two circumferential steps (104b) that provide support for both the filter plate and the graft frame. The base frame (100) shown in FIG. 3B also comprises at least one recess (109) and an extended lip (110), the extended lip (110) comprises at least one hook (112) to be accommodated in the at least one niche of a second compression system. Furthermore, the circumferential wall (102) comprises a plurality of drain channels (111).

Figure 4A:
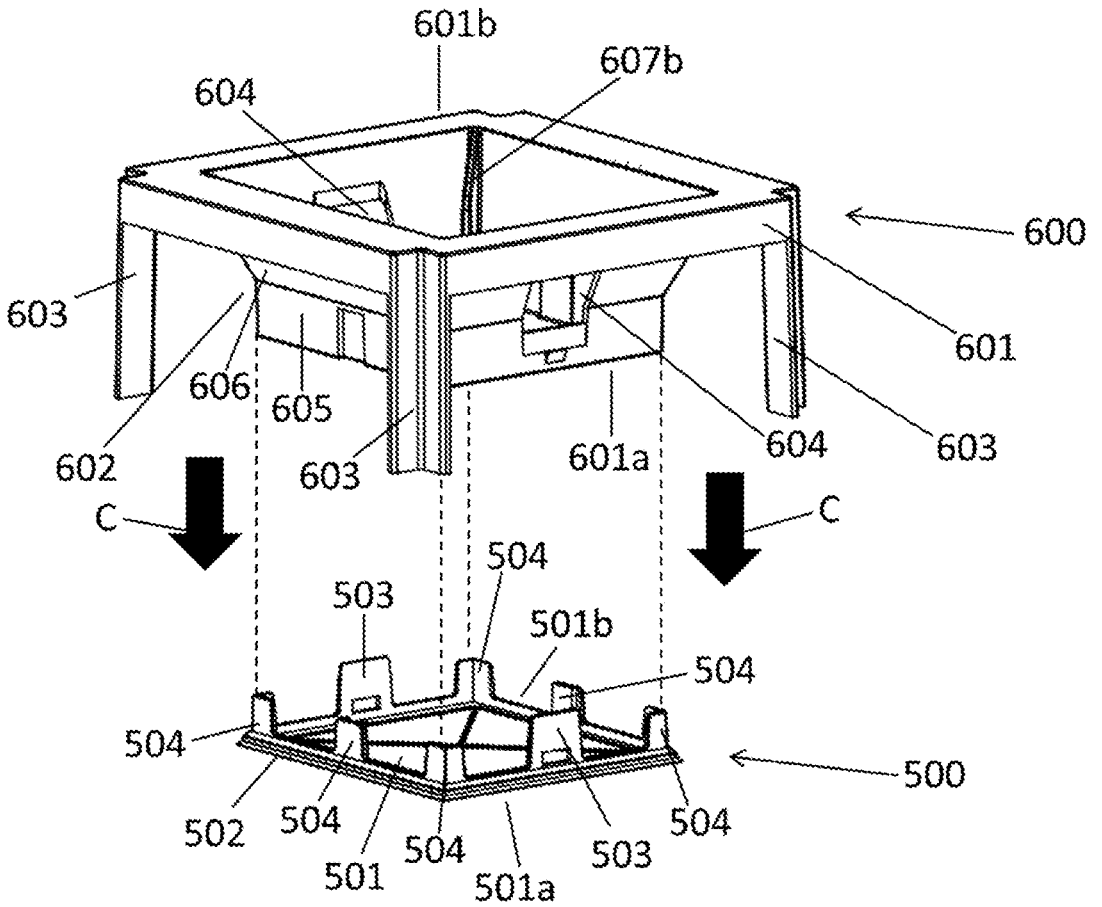
FIG. 4A shows an upper perspective view of a piston assembly comprising a piston (500) and a piston frame (600) according to one embodiment of the invention.
Figure 4B:
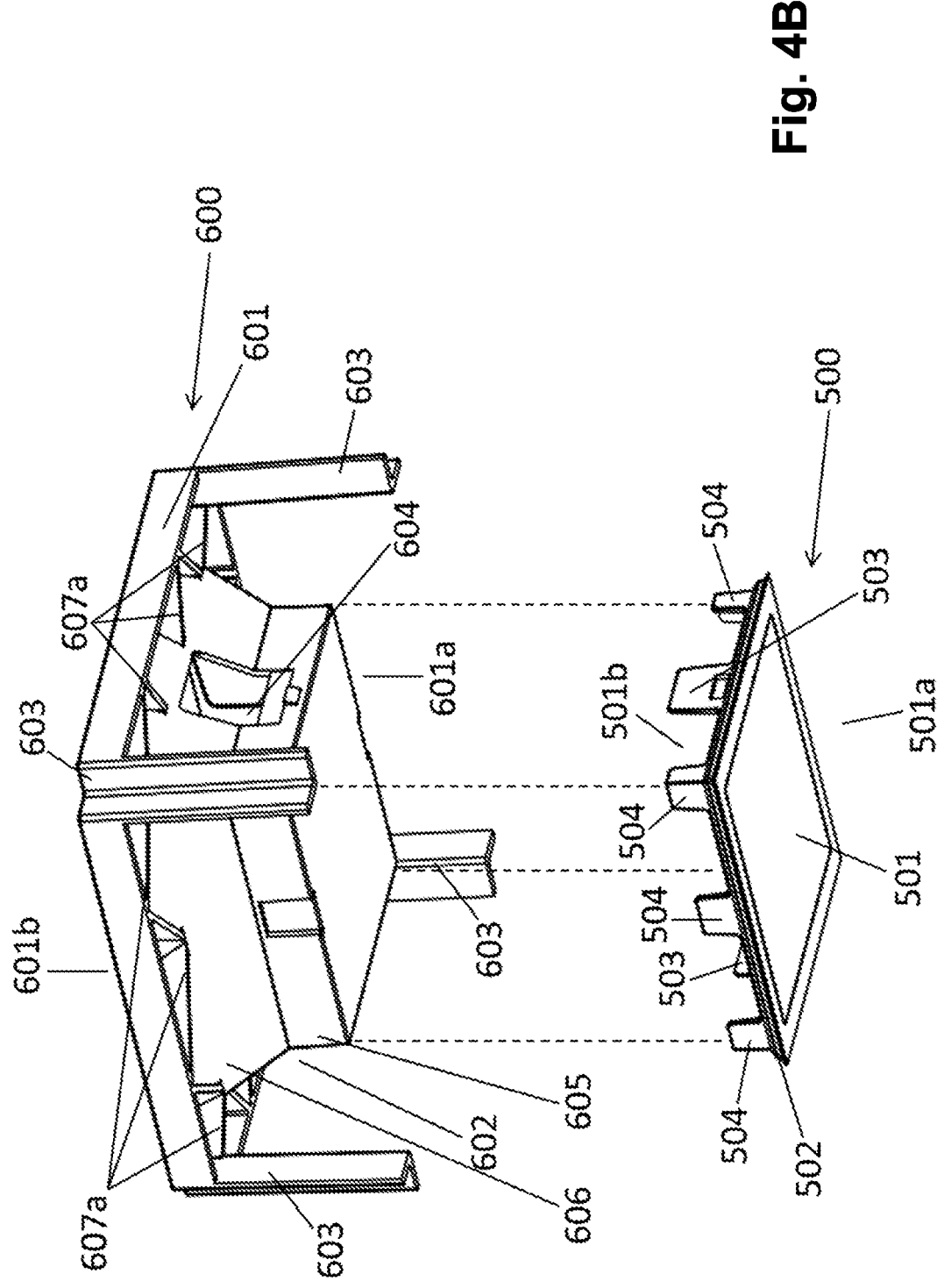
FIG. 4B shows a bottom perspective view of a piston assembly comprising a piston (500) and a piston frame (600) according to one embodiment of the invention.

FIGS. 4A and 4B respectively show an upper and bottom perspective views of a piston assembly comprising a piston (500) and a piston frame (600) according to one embodiment of the invention. As shown in FIGS. 4A and 4B, in the operating mode, the piston frame (600) is configured to press the piston along the compression direction (C) against the hydrogel layer. The piston frame (600) comprises a frame member (601), a support structure (602) protruding from a first side (601a) of the frame member (601) and a plurality of guiding extensions (603) protruding from an edge of the frame member (601) in the compression direction (C), such that each extension (603) is associated to one of the indentations (103). Accordingly, at the first side (601a) of the frame member (601), the support structure (602) holds the piston (500), while at the second side (601b) of the frame member (601) the support structure (602) forms a receptacle for accommodating one or more compression weights. The support structure (602) comprises a support base (605), which forms a contact surface with the piston base (501), and a circumferential support wall (606) connecting the support base (605) to the frame member (601). The support structure (602) is further connected to the frame member (601) at the first side (601a) of said frame member (601) by stabilizing elements (607a). The piston frame (600) also comprises stabilizing elements (607b) at the second side (601b) of the frame member (601).

According to the embodiment shown in FIGS. 4A and 4B, the piston (500) comprises a plate-like piston base (501), such that a first side (501a) of the piston base (501) forms a contact surface with the hydrogel layer during compression. The piston base (501) also comprises a circumferential edge region (502) designed to contact the circumferential frame member of the graft frame when pressing against the hydrogel layer. The piston (500) comprises two latching elements (503) protruding from edge region (502) on a second side (501b) of the piston base (501). The latching elements (503) are designed to be associated with corresponding apertures (604) on the support structure (602) of the piston frame (600). The latching elements (503) are accessible from a second side (601b) of the piston frame (600). The piston (500) also comprises guiding elements (504) protruding from the edge region (502) on said second side (501b) of the piston base (501), said guiding elements (504) are designed to slide along said support base (602).

Figure 5:
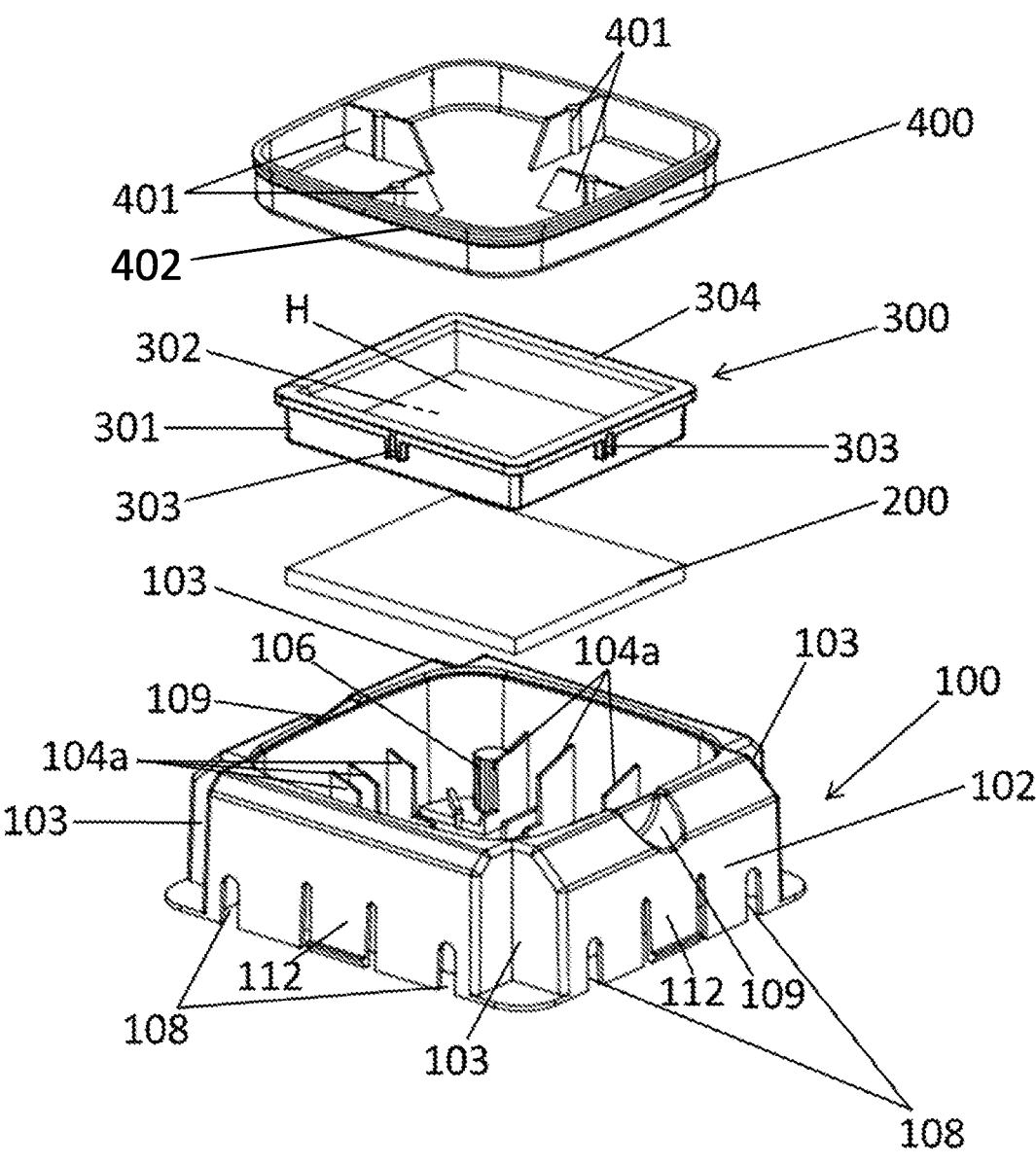
FIG. 5 is a perspective exploded view of the system during hydrogel polymerization (namely, the hydrogel polymerization assembly), according to one embodiment of the invention.

FIG. 5 is a perspective exploded view of the system during hydrogel polymerization (namely, the hydrogel polymerization assembly), the system comprising a hydrogel receptacle assembly and a removable lid according to one embodiment of the invention.

The hydrogel receptacle assembly comprises a base frame (100) as described in FIG. 3A, a filter plate (200) and a graft frame (300). The graft frame (300) comprises a circumferential frame member (301) and a permeable membrane bottom (302), and is configured to accommodate a hydrogel layer (H). The circumferential frame member (301) comprises an upper edge (304) and a region (303) designed to fit snugly between two of the plurality of steps (104a). According to the embodiment shown in FIG. 5, the lid (400) comprises four gripping elements (401) and a circumferential sealing gasket (402).

Figure 6A:
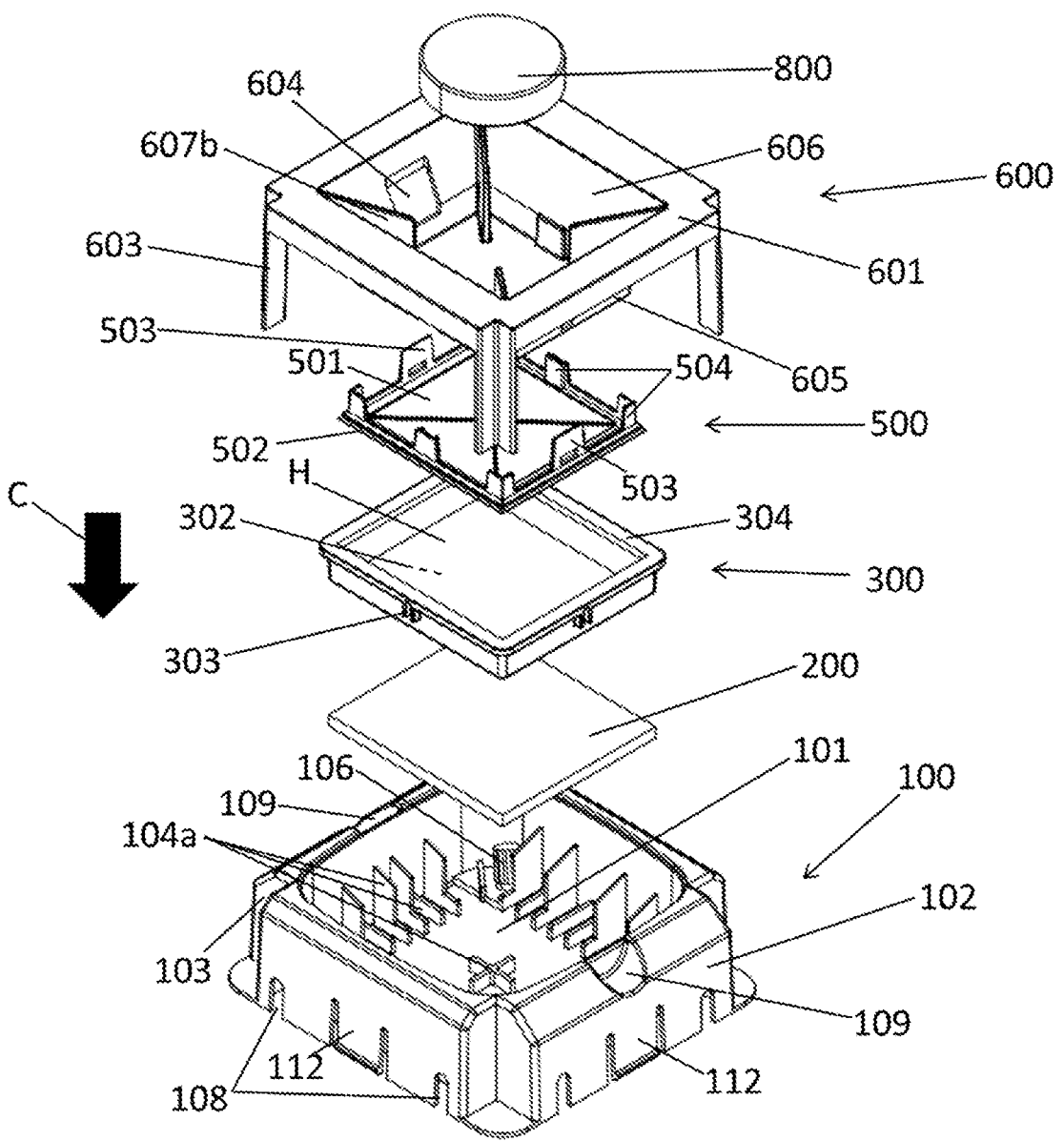
FIG. 6A is a perspective exploded view of the system during compression of the hydrogel (namely, the compression assembly), according to one embodiment of the invention.

FIG. 6A is a perspective exploded view of the system during compression of the hydrogel (namely, the compression assembly), the system comprising a hydrogel receptacle assembly, a piston assembly and a compression weight, according to one embodiment of the invention. The hydrogel receptacle assembly comprises a base frame (100) as described in FIG. 3A, a filter plate (200) and a graft frame (300) as described in FIG. 5. The piston assembly comprises a piston (500) and a piston frame (600) as described in FIGS. 4A and 4B. The system in the compression operating mode also comprises one or more compression weights (800).

Figure 6B:
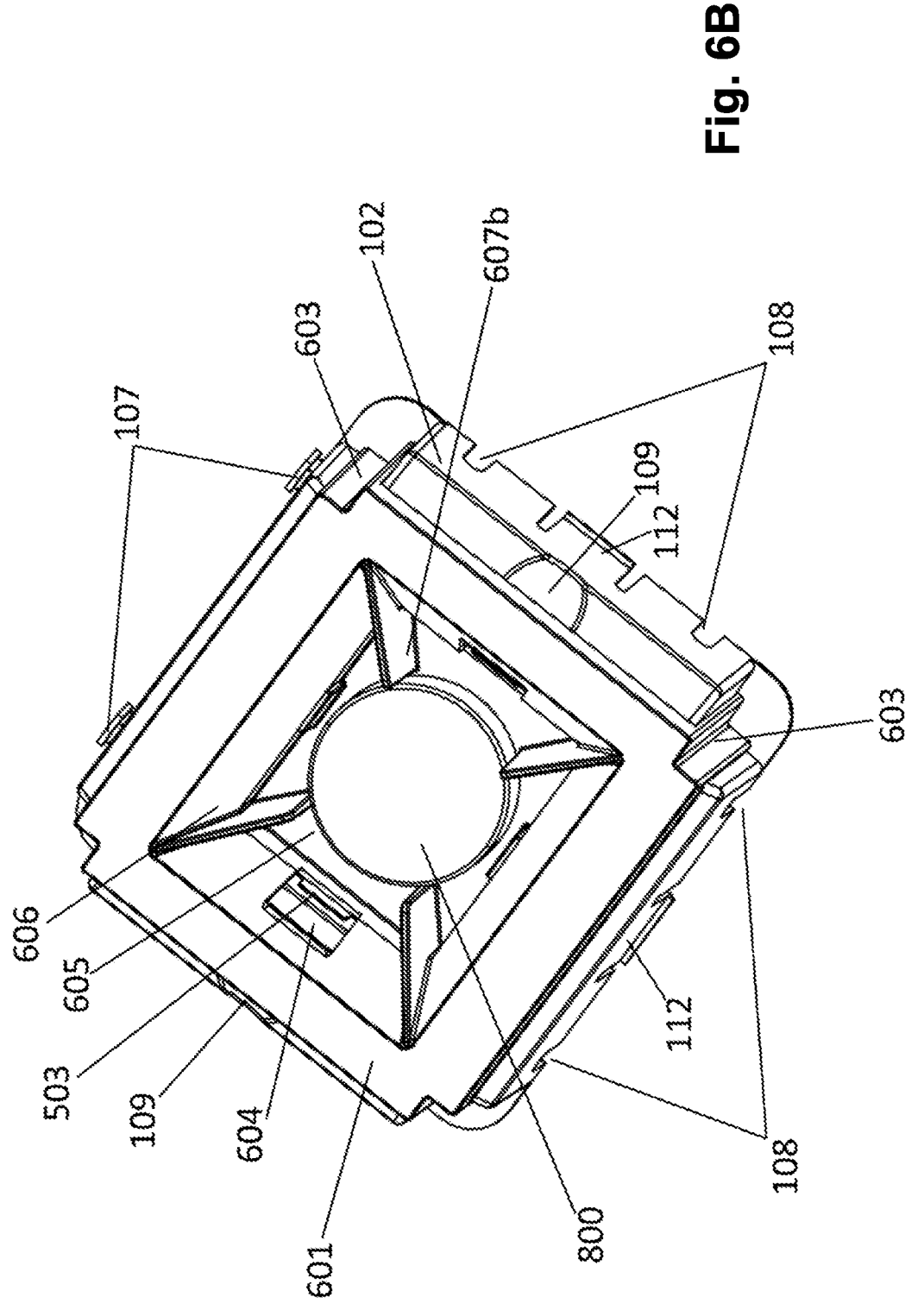
FIG. 6B is a perspective view of the system during compression of the hydrogel (namely, the compression assembly), as shown in FIG. 6A.

FIG. 6B is a perspective view of the system during compression of the hydrogel (namely, the compression assembly), as described in FIG. 6A.

Figure 7A:
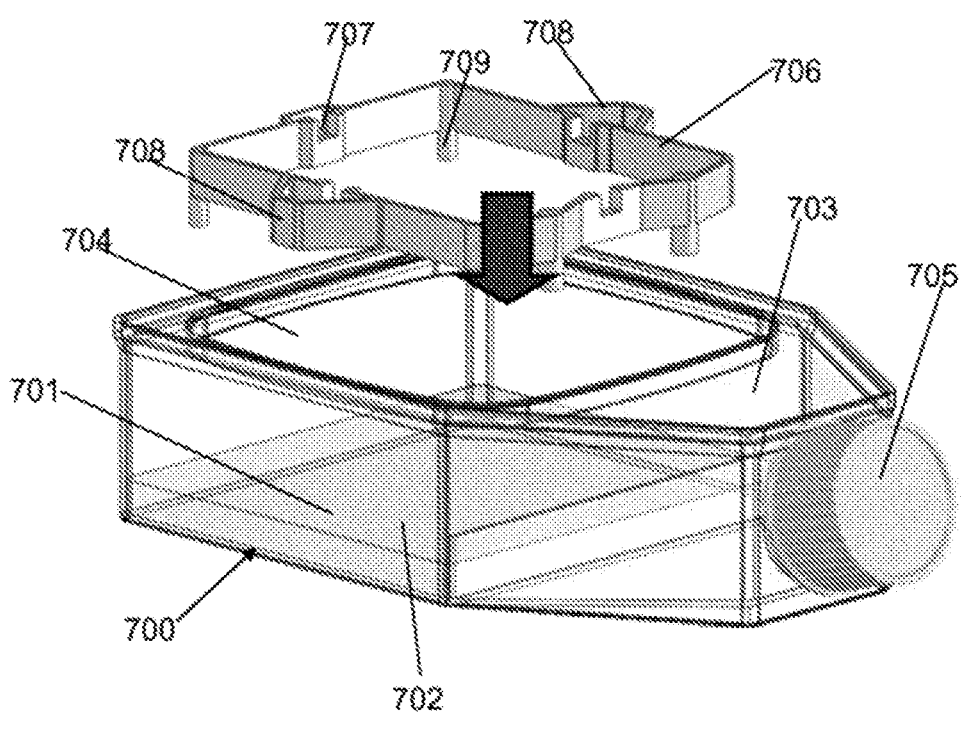
FIGS. 7A-7C show a perspective view of the flask and the support frame used for further incubating the compressed hydrogel residing in the graft frame, according to one embodiment of the invention.
Figure 7B:
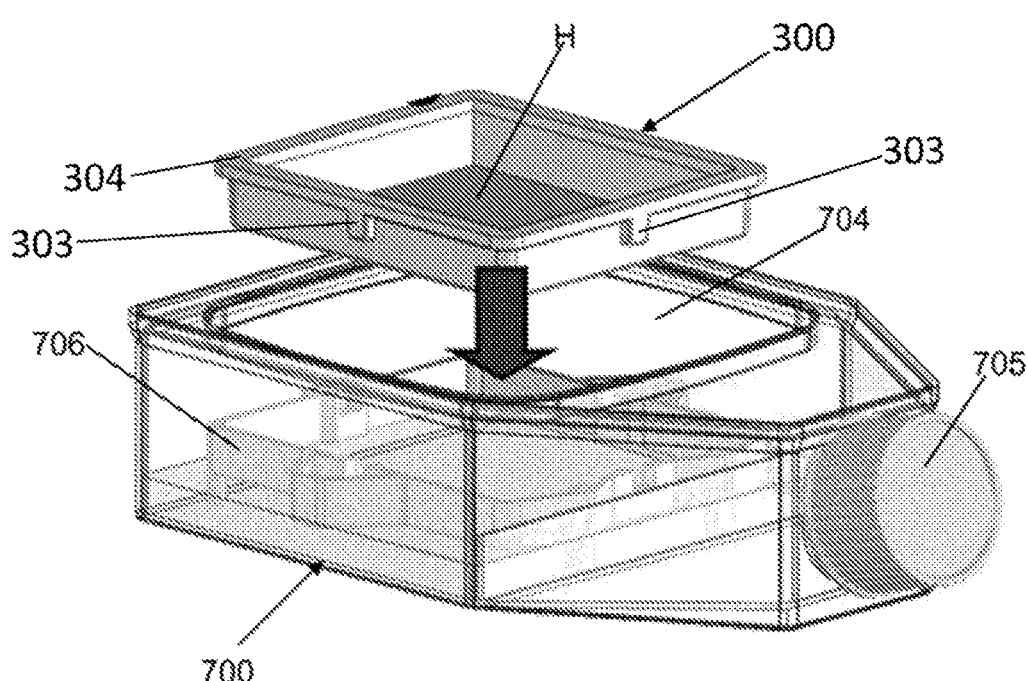
Figure 7C:
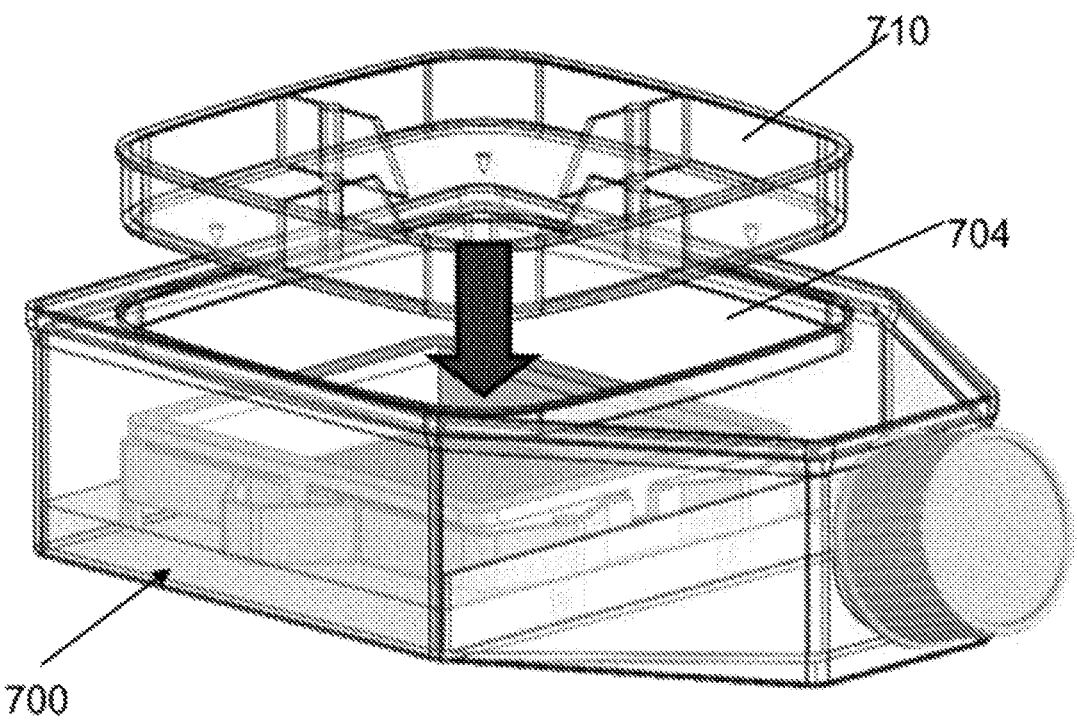

FIGS. 7A-7C are a perspective view of the flask used to incubate the compressed hydrogel layer. The flask (700) is designed to receive the graft frame (300) carrying the compressed hydrogel layer (H). The flask (700) comprises a top opening (704) located on the upper wall (703) of the flask (700), and a further opening for liquid handling, wherein a screw cap (705) is provided for closing said further opening. The flask (700) also comprises a lid (710) that is designed to close top opening (704).

As shown in FIGS. 7A-7C, the support frame (706) provides a resting place for the graft frame (300) inside the flask (700). The support frame shown in FIGS. 7A-7C comprises recesses (707) formed in an upper edge of the support frame (706) for receiving said region (303) of the circumferential frame member (301) of the graft frame (300), wherein the graft frame is designed to rest with its upper edge (304) on the upper edge of the support frame (706). The support frame (706) rests with four stands (709) on the bottom (701) of the flask (700). The support frame (706) further comprises two opposing protruding regions (708) for contacting a wall (702) of the flask (700) from the interior of the flask (700).

The invention claimed is:

1. A disposable system for preparing a compressed hydrogel, the system comprising:

(a) a hydrogel receptacle assembly, comprising:

(i) a graft frame (300) configured to accommodate a hydrogel layer (H); the graft frame (300) comprising a circumferential frame member (301) and a permeable membrane bottom (302) connected to said frame member (301);

(ii) a porous filter plate (200); and (iii) a base frame (100), comprising a bottom wall (101); a circumferential wall (102) extending from the bottom wall (101), so that the base frame (100) forms a container that is configured to receive the filter plate (200) and the graft frame (300) in an operating mode, such that the filter plate (200) is arranged between the bottom wall (101) of the base frame (100) and the membrane bottom (302) of the graft frame (300); and a plurality of indentations (103) located at one or more edges of the base frame (100);

(b) a removable lid (400); and (c) a piston assembly comprising:

(i) a piston frame (600), comprising a frame member (601); a support structure (602) extending from a first side (601a) of the frame member (601) towards the membrane bottom (302) in the operating mode; and a plurality of guiding extensions (603) protruding from an edge of the frame member (601) in the compression direction (C); the piston frame (600) is configured to be slidably arranged on the base frame (100) in the operating mode, such that each extension (603) is associated to one of the indentations (103), so that the piston frame (600) is guided by said extensions (603) onto the base frame (100) along the compression direction (C); and (ii) a piston (500) configured to be connected to the piston frame (600) in a releasable manner, such that in the operating mode the piston frame (600) is configured to press the piston (500) along the compression direction (C) against the hydrogel layer (H) residing in the graft frame (300) so as to compress the hydrogel layer (H) between the piston (500) and the membrane bottom (302) of the graft frame (300);

wherein the graft frame (300), the base frame (100), the filter plate (200), the lid (400), the piston (500) and the piston frame (600) are disposable; and wherein the graft frame (with the exception of the membrane bottom) and the piston frame as well as at least one member of the group consisting of the base frame and the tray comprise polyether ether ketone (PEEK).

2. The disposable system according to claim 1, comprising:

a transport grid between said graft frame and said removable lid.

3. The disposable system according to claim 1, wherein the piston comprises polypropylene.

4. The disposable system according to claim 1, wherein at least one member of the group consisting of the base frame, the graft frame, the piston frame and the piston plate comprise at least one member of the group consisting of polycarbonate (PC), polystyrene (PS), and methyl methacrylate-acrylonitrile-butadiene-styrene (MABS).

5. The disposable system according to claim 1, wherein the base frame comprises a ledge on which the filter plate rests and/or a ledge, on which an upper edge of the circumferential frame member of the graft frame rests.

6. The disposable system according to claim 5, wherein the ledge comprises at least one single circumferential step on the circumferential wall of the base frame.

7. The disposable system according to claim 5, wherein the ledge comprises a plurality of steps, such that each step of the plurality of steps provides support to at least one of the components of the systems.

8. The disposable system according to claim 5, wherein the ledge comprises a combination of the circumferential step and a plurality of steps.

9. The disposable system according to claim 6, wherein the circumferential step comprises at least one recess for receiving a region of the frame member of the graft frame in a form-fitting manner in order to prevent any unintentional movement of the graft frame resting within the base frame during compression.

10. The disposable system according to claim 1, wherein the filter comprises a sintered polymer.

11. The disposable system according to claim 1, wherein the membrane bottom consists of polyethylene terephthalate (PET).

* * * * *